United States Patent
Utsunomiya et al.

(10) Patent No.: US 9,556,307 B2
(45) Date of Patent: Jan. 31, 2017

(54) METHOD FOR PRODUCING POLYBUTYLENE TEREPHTHALATE

(71) Applicants: MITSUBISHI CHEMICAL CORPORATION, Chiyoda-ku (JP); GENOMATICA, INC., San Diego, CA (US)

(72) Inventors: Masaru Utsunomiya, Tokyo (JP); Yusuke Izawa, Mie (JP); Norikazu Konishi, Mie (JP); Shinichiro Matsuzono, Mie (JP); Takayuki Suzuki, Mie (JP); Michael Japs, San Diego, CA (US); Mark Burk, San Diego, CA (US); Warren Clark, Lake Jackson, TX (US)

(73) Assignees: MITSUBISHI CHEMICAL CORPORATION, Chiyoda-ku (JP); Genomatica, Inc., San Diego, CA (US)

( * ) Notice: Subject to any disclaimer, the term of this patent is extended or adjusted under 35 U.S.C. 154(b) by 0 days.

(21) Appl. No.: 14/560,800

(22) Filed: Dec. 4, 2014

(65) Prior Publication Data

US 2015/0087034 A1 Mar. 26, 2015

Related U.S. Application Data

(63) Continuation of application No. PCT/JP2013/065365, filed on Jun. 3, 2013.

(30) Foreign Application Priority Data

Jun. 5, 2012 (JP) ................. 2012-128064

(51) Int. Cl.
| | |
|---|---|
| C12P 7/62 | (2006.01) |
| C08G 63/00 | (2006.01) |
| C08G 63/80 | (2006.01) |
| C08G 63/183 | (2006.01) |
| C08G 63/78 | (2006.01) |
| C12P 7/18 | (2006.01) |
| C12N 9/04 | (2006.01) |
| C12N 9/02 | (2006.01) |
| C12N 9/00 | (2006.01) |

(52) U.S. Cl.
CPC ............ *C08G 63/80* (2013.01); *C08G 63/183* (2013.01); *C08G 63/78* (2013.01); *C12N 9/0006* (2013.01); *C12N 9/0008* (2013.01); *C12N 9/93* (2013.01); *C12P 7/18* (2013.01); *C12Y 101/01061* (2013.01); *C12Y 102/01024* (2013.01); *C12Y 102/04002* (2013.01); *C12Y 602/01004* (2013.01); *Y02P 20/52* (2015.11)

(58) Field of Classification Search
None
See application file for complete search history.

(56) References Cited

U.S. PATENT DOCUMENTS

| 6,486,367 B1 | 11/2002 | Budge et al. |
|---|---|---|
| 2007/0275242 A1 | 11/2007 | Gopal et al. |
| 2008/0039571 A1 | 2/2008 | Cohoon et al. |
| 2009/0075351 A1 | 3/2009 | Burk et al. |
| 2012/0046427 A1 | 2/2012 | Cooper et al. |
| 2012/0094345 A1 | 4/2012 | Burk et al. |
| 2012/0122171 A1 | 5/2012 | Burk et al. |
| 2013/0196397 A1 | 8/2013 | Burk et al. |
| 2015/0087038 A1 | 3/2015 | Utsunomiya et al. |
| 2015/0087789 A1 | 3/2015 | Utsunomiya et al. |

FOREIGN PATENT DOCUMENTS

| CN | 101668861 A | 3/2010 |
|---|---|---|
| EP | 2 857 377 A1 | 4/2015 |
| JP | 11-240846 A | 9/1999 |
| JP | 2006-328380 A | 12/2006 |
| JP | 2008-101143 | * 5/2008 |
| JP | 2008-101143 A | 5/2008 |
| WO | WO 2007/089653 A2 | 8/2007 |
| WO | WO 2008/115840 A2 | 9/2008 |
| WO | WO 2008/115840 A3 | 9/2008 |
| WO | WO 2012/024112 A1 | 2/2012 |
| WO | WO 2013/005749 A1 | 1/2013 |
| WO | WO 2013/183593 A1 | 12/2013 |

OTHER PUBLICATIONS

Extended European Search Report issued Apr. 28, 2015 in Patent Application No. 13800602.8.
International Search Report issued Aug. 20, 2013 in PCT/JP2013/065365 (with English language translation).
International Preliminary Report on Patentability and Written Opinion issued Dec. 9, 2014 in PCT/JP2013/065365 (with English language translation).
Office Action issued May 27, 2016 in European Patent Application No. 13 800 602.8.
Combined Office Action and Search Report issued Oct. 20, 2015 in Chinese Patent Application No. 201380041733.3 (with partial English language translation and English translation of categories of cited documents).
Australian Office Action issued on Jan. 20, 2016 in Patent Application No. 2013272713.
Office Action issued on Mar. 29, 2016 in Eurasian Patent Application No. 201492263 (with English language translation).
Combined Chinese Office Action and Search Report issued Apr. 15, 2016 in Patent Application No. 201380041733.3 (with English language translation).
Third Office Action issued Oct. 26, 2016, in Chinese patent application No. 201380041733.3.

* cited by examiner

*Primary Examiner* — Iqbal H Chowdhury
(74) *Attorney, Agent, or Firm* — Oblon, McClelland, Maier & Neustadt, L.L.P.

(57) ABSTRACT

The present invention aims to provide a method for producing polybutylene terephthalate (PBT) with an excellent color using biomass-derived 1,4-butanediol (BG). The invention relates to a method for producing PBT comprising a step of subjecting a diol component containing raw material 1,4-BG having a nitrogen content of 0.01 to 50 ppm by mass and a dicarboxylic acid component to esterification or ester-exchange reaction, and a polycondensation reaction step for obtaining PBT from the reactant, wherein the content of gamma butyrolactone in the raw material 1,4-BG is 1 to 100 ppm by mass.

15 Claims, 1 Drawing Sheet

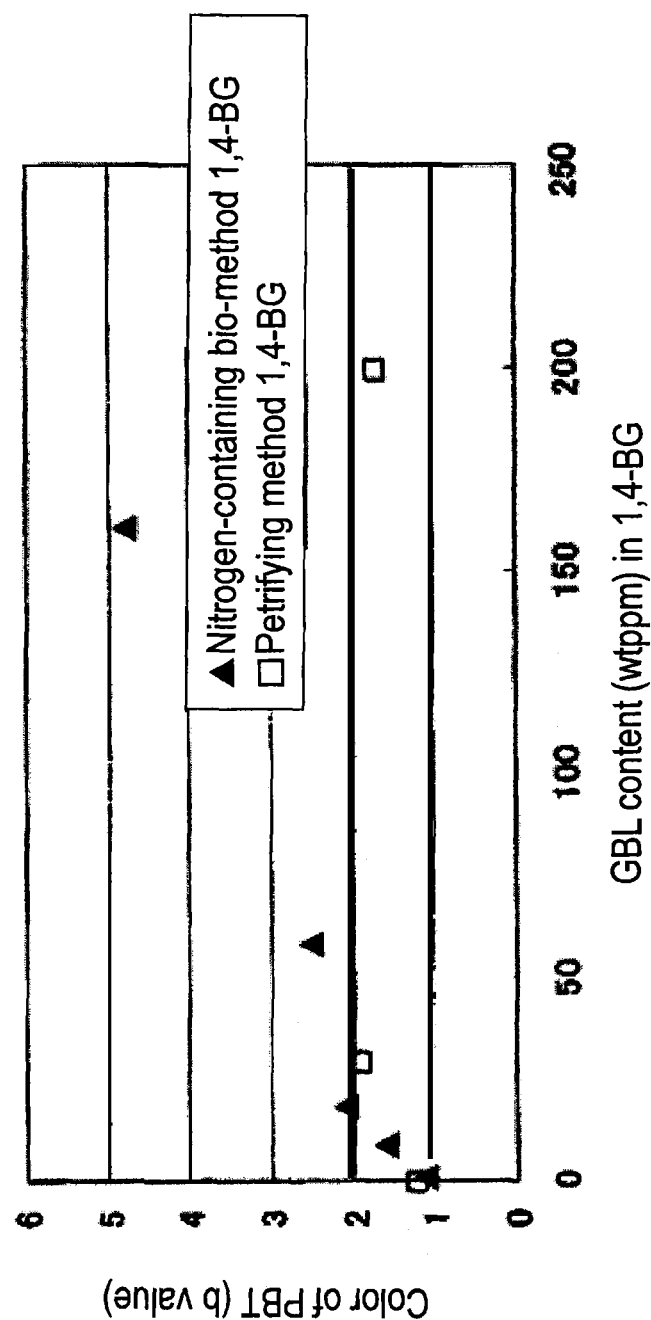

METHOD FOR PRODUCING POLYBUTYLENE TEREPHTHALATE

TECHNICAL FIELD

The present invention relates to a method for producing polybutylene terephthalate with an excellent color from biomass-derived 1,4-butanediol as a raw material.

BACKGROUND ART

Polybutylene terephthalate (hereinafter sometimes abbreviated as "PBT"), which is a typical engineering plastic among thermoplastic polyester resins, is excellent in view of the easy molding process, mechanical property, heat resistance, chemical resistance, aroma retention property, and other physical and chemical properties. Thus, PBT has been widely used as a material for injection-molded parts such as automotive parts, electric and electronic parts, and parts for a precision instrument. Recently, as PBT has been widely used also in the field of general consumer goods such as a film, a sheet, a monofilament and fibers making use of its excellent properties, PBT with an excellent color has been required.

PBT can be generally obtained by reacting terephthalic acid or an alkyl ester thereof with 1,4-butanediol (hereinafter sometimes abbreviated as "1,4-BG"). However, since 1,4-BG is easily converted into tetrahydrofuran (hereinafter sometimes abbreviated as "THF") during the reaction, a method for producing PBT in high yield in which the conversion of 1,4-BG into THF is prevented is required.

In addition, with the growing demand for building a sustainable society, it is desired to switch from materials derived from fossil fuel in the production of PBT as in the energy production. When no fossil fuel is used as a raw material, a biomass-derived material obtained from plants and the like as raw materials is one of the possible raw materials. Also with regard to 1,4-BG, which is a raw material of PBT, a method for producing PBT from biomass-derived 1,4-BG as a raw material has been studied.

However, the color of obtained PBT deteriorates when biomass-derived raw material 1,4-BG is used, in comparison with the color of PBT produced from raw material 1,4-BG which is obtained from fossil fuel such as petroleum. The major cause for the color deterioration is thought to be a nitrogen-containing component in PBT. In addition, it is thought that components other than this component also have an influence on the color of PBT.

PTL 1 describes a technique for obtaining PBT from a biomass-derived raw material and describes that PBT with a nitrogen content of 50 ppm by mass or less is obtained by setting the nitrogen content in the biomass-derived raw material 1,4-BG within 0.01 to 50 ppm by mass. PTL 1 also describes that, although 1-acetoxy-4-hydroxybutane (hereinafter sometimes abbreviated as "1,4-HAB") contained in the raw material 1,4-BG delays the polycondensation reaction of PBT and causes the coloration of PBT, the coloration of PBT due to delayed polymerization can be reduced by using, as a raw material, 1,4-BG obtained from raw material 1,4-BG with a controlled nitrogen concentration.

In addition, it is known that gamma butyrolactone (hereinafter sometimes abbreviated as "GBL") is generated as a by-product in the conventional methods for producing 1,4-BG. For example, PTL 2 describes that gamma butyrolactone is produced as a by-product when a crude hydrogenated product containing 1,4-BG is obtained by hydrogenating maleic acid, succinic acid, maleic anhydride, fumaric acid and/or the like, in a method for producing 1,4-BG from a raw material derived from fossil fuel.

As methods for producing 1,4-BG from a biomass-derived raw material, PTL 3 describes to subject biomass-derived succinic acid to chemical reduction or bioengineering hydrogenation to produce 1,4-BG, and PTL 4 describes a method for obtaining 1,4-BG by direct fermentation from bacterial cells.

CITATION LIST

Patent Literatures

PTL 1: JP-A-2008-101143 (the term "JP-A" as used herein means an "unexamined published Japanese patent application")
PTL 2: JP-A-11-240846
PTL 3: JP-A-2009-077719
PTL 4: JP-T-2010-521182 (the term "JP-T" as used herein means a published Japanese translation of a PCT patent application)

SUMMARY OF INVENTION

Technical Problem

However, in the method described in PTL 3, the production of by-product GBL is highly likely to proceed because hydrogenation is similarly conducted as in the method of PTL 2. In addition, in the method of PTL 4, GBL is highly likely to be generated as a by-product through a metabolic pathway and the like.

Furthermore, PTL 1 to PTL 4 above do not describe the relation between gamma butyrolactone and the nitrogen-containing compound contained in the raw material 1,4-BG.

Moreover, it was found that, even if the content of the nitrogen-containing compound in the raw material 1,4-BG was controlled in order to prevent the coloration of PBT, which is caused by delayed polymerization due to 1,4-HAB in the raw material 1,4-BG the unnecessary coloration of PBT could not be always prevented although delayed polymerization could be prevented.

The invention was made in view of the above problems and an object thereof is to provide a method for producing PBT with an excellent color efficiently from biomass-derived 1,4-BG as a raw material.

Solution to Problem

In order to solve the problems described above, the present inventors made extensive and intensive investigations. As a result, the inventors found that a compound is generated by the reaction of gamma butyrolactone contained in the raw material 1,4-BG with a nitrogen-containing compound in the raw material 1,4-BG during the PBT production, and this compound causes the further coloration of PBT. In addition, the inventors found that PBT with an excellent color can be obtained by setting the content of gamma butyrolactone in 1,4-BG to a specific amount when PBT is produced from 1,4-BG containing the nitrogen-containing compound. Thus, the invention was completed.

That is, the gist of the invention resides in the following items [1] to [6].

[1] A method for producing polybutylene terephthalate comprising a step (a) of subjecting a diol component containing biomass-derived raw material 1,4-butanediol having a nitrogen content of 0.01 to 50 ppm by mass and a dicarboxylic acid component containing terephthalic acid or an alkyl terephthalate to esterification reaction or ester-exchange reaction, and a polycondensation reaction step (b) of subjecting the reactant obtained in the step (a) to polycondensation reaction and obtaining polybutylene terephthalate, wherein the content of gamma butyrolactone in the raw material 1,4-butanediol is 1 to 100 ppm by mass.

[2] The method for producing polybutylene terephthalate described in the above [1] which further comprises a step of obtaining the raw material 1,4-butanediol by purifying biomass-derived crude 1,4-butanediol, wherein the step is conducted before the step (a).

[3] The method for producing polybutylene terephthalate described in the above [2], wherein the content of gamma butyrolactone in the crude 1,4-butanediol is 101 ppm by mass to 2% by mass.

[4] The method for producing polybutylene terephthalate described in any one of the above [1] to [3], wherein the content of 1-acetoxy-4-hydroxybutane in the raw material 1,4-butanediol is 1 to 99 ppm by mass.

[5] The method for producing polybutylene terephthalate described in any one of the above [1] to [4] which further comprises a step of directly producing the raw material 1,4-butanediol or the crude 1,4-butanediol from at least one carbon source selected from the group consisting of glucose, fructose, xylose and saccharose by a fermentation method.

[6] The method for producing polybutylene terephthalate described in any one of the above [1] to [5] which further comprises a step of producing the raw material 1,4-butanediol or the crude 1,4-butanediol from a biomass material using the following non-natural microorganism biocatalyst:

non-natural microorganism biocatalyst: a microorganism biocatalyst which contains a microorganism containing at least one extrinsic nucleic acid fragment coding 4-hydroxybutanoic acid dehydrogenase, succinyl-CoA synthetase, CoA-dependent succinate-semialdehyde dehydrogenase or α-ketoglutarate decarboxylase and having 4-hydroxybutanoic acid biosynthesis pathway and in which the microorganism contains the extrinsic nucleic acid fragment in an amount sufficient to secrete a monomer of 4-hydroxybutanoic acid.

Advantageous Effects Of Invention

According to the invention, PBT with an excellent color can be efficiently produced from biomass-derived 1,4-BG as a raw material.

BRIEF DESCRIPTION OF DRAWINGS

FIG. 1 is a FIGURE showing the correlation between the colors of PBT obtained by the method for producing PBT of the invention (nitrogen-containing bio-method) and conventional methods for producing PBT (petrifying methods) and the GBL contents in the raw material 1,4-BG.

DESCRIPTION OF EMBODIMENTS

The present invention is described in detail below, but the respective constituent requirements described below are a representative example of the embodiment of the present invention, and the present invention is not limited to them. Incidentally, a numerical range expressed by using the expression "(numerical value) to (numerical value)" in the description of the present invention means a range which includes the numerical values before and after "to" as a lower limit and an upper limit, respectively. In addition, a lower limit or an upper limit in the description of the present invention means a range which includes a numerical value of the lower limit or the upper limit.

Incidentally, in the description of the present invention, the expression "wt %", "ppm by weight", "parts by weight" and "weight ratio" have the same meanings as "mass %", "ppm by mass", "parts by mass" and "mass ratio", respectively. Also, when simply referred to as "ppm", this indicates "ppm by weight".

<Raw Materials for Producing PBT>

In the invention, PBT is obtained by: subjecting a dicarboxylic acid component containing terephthalic acid or an alkyl terephthalate and a diol component containing biomass-derived raw material 1,4-butanediol to esterification reaction or ester-exchange reaction; and then subjecting the reactant to polycondensation reaction. In this regard, an alkyl group having 1 to 3 carbon atoms is preferable as the alkyl group of the alkyl terephthalate.

The content of terephthalic acid or the alkyl terephthalate used as the raw material is preferably 80% by mol or more of the whole dicarboxylic acid component, and the content is further preferably 90% by mol or more and most preferably 100% by mol.

The content of the biomass-derived raw material 1,4-BG is preferably 80% by mol or more of the whole diol component, and the content is further preferably 90% by mol or more and particularly preferably 99% by mol or more.

It is preferable that the percentage of terephthalic acid or the alkyl terephthalate content in the whole dicarboxylic acid component and the percentage of the biomass-derived 1,4-BG content in the whole diol component are not less than the above lower limits, because the molded part is likely to be excellent in the mechanical strength, heat resistance, aroma retention property and the like, in view of the crystallization when the material is molded into an electric part or the like, or in view of the orientational crystallization of the molecular chains by stretching when the material is molded into a film, fibers or the like.

The dicarboxylic acid component as the raw material may contain another dicarboxylic acid component in addition to terephthalic acid or the alkyl terephthalate as the main component, and it is also possible to add another dicarboxylic acid component to the reactor with terephthalic acid or the alkyl terephthalate.

Examples of the other dicarboxylic acid component are: aromatic dicarboxylic acids such as phthalic acid, isophthalic acid, dibromoisophthalic acid, sodium sulfoisophthalate, phenylenedioxydicarboxylic acid, 4,4'-diphenyldicarboxylic acid, 4,4'-diphenylether dicarboxylic acid, 4,4'-diphenylketone dicarboxylic acid, 4,4'-diphenoxyethane dicarboxylic acid, 4,4'-diphenylsulfone dicarboxylic acid and 2,6-naphthalenedicarboxylic acid, and ester-forming derivatives thereof; alicyclic dicarboxylic acids such as hexahydro terephthalic acid and hexahydro isophthalic acid, and ester-forming derivatives thereof; and aliphatic chain dicarboxylic acids such as succinic acid, glutaric acid, adipic acid, pimelic acid, suberic acid, azelaic acid, sebacic acid, undecadicarboxylic acid and dodecadicarboxylic acid, and ester-forming derivatives thereof. A kind of these components may be used alone or a mixture of two or more kinds thereof may be used.

The diol component as the raw material may contain another diol component in addition to the biomass-derived raw material 1,4-BG, and it is also possible to add another diol component to the reactor with the biomass-derived raw material 1,4-BG.

Examples of the other diol component are: aliphatic chain diols such as ethylene glycol, trimethylene glycol, pentamethylene glycol, hexamethylene glycol, octamethylene glycol, decamethylene glycol, neopentyl glycol, 2-methyl-1,3-propanediol, 1,2-butanediol, 1,3-butanediol, 2,3-butanediol, 1,3-pentanediol, 2,3-pentanediol, 2-ethyl-2-butyl-1,3-propanediol, polyethylene glycol and polytetramethylene glycol; alicyclic diols such as 1,2-cyclohexanediol, 1,4-cyclohexanediol, 1,1-cyclohexanedimethylol, 1,4-cyclohexanedimethylol and 2,5-norbornanedimethylol; aromatic diols such as xylylene glycol, 4,4'-dihydroxybiphenyl, 2,2-bis(4'-hydroxyphenyl)propane, 2,2-bis(4'-β-hydroxyethoxyphenyl)propane, bis(4-hydroxyphenyl)sulfone and bis(4'-β-hydroxyethoxyphenyl)sulfonic acid; an ethylene oxide adduct or a propylene oxide adduct of 2,2-bis(4'-hydroxyphenyl)propane; and 1,4-BG other than biomass-derived 1,4-BG. A kind of these components may be used alone or a mixture of two or more kinds thereof may be used.

As the PBT raw materials, the following components may be further used as the copolymerization components in addition to the above dicarboxylic acid component and the diol component.

Examples of the copolymerization components are hydroxyl carboxylic acids such as glycolic acid, p-hydroxybenzoic acid and p-β-hydroxyethoxybenzoic acid, monofunctional components such as alkoxy carboxylic acid, stearyl alcohol, heneicosanol, octacosanol, benzyl alcohol, stearic acid, behenic acid, benzoic acid, t-butylbenzoic acid and benzoylbenzoic acid, and tri- to polyfunctional components such as tricarballylic acid, trimellitic acid, trimesic acid, pyromellitic acid, naphthalenetetracarboxylic acid, gallic acid, trimethylolethane, trimethylolpropane, glycerol, pentaerythritol and sugar ester. A kind of these copolymerization components may be used alone or a mixture of two or more kinds thereof may be used.

<Biomass-Derived Raw Material 1,4-BG>

The raw material 1,4-BG used for producing PBT in the invention is biomass-derived 1,4-BG and is preferable in terms of the environmental protection.

The biomass material includes a material in which light energy of the sun is converted into a form of starch, cellulose or the like by photonic synthesis of a plant and stored, the body of an animal which grows by eating plants, a product obtained by processing a plant body or an animal body and the like.

Specifically, wood, paddy straw, rice bran, old rice, corn, sugar cane, cassava, sago palm, soy pulp, corncobs, tapioca refuse, bagasse, vegetable oil refuse, potatoes, buckwheat, soybeans, fat, old papers, papermaking residues, fishery product residues, excreta from domestic animals, sewage sludge, food wastes and the like are mentioned. Among them, plant materials such as wood, paddy straw, old rice, corn, sugar cane, cassava, sago palm, soy pulp, corncobs, tapioca refuse, bagasse, vegetable oil refuse, potatoes, buckwheat, soybeans, fat, old papers and papermaking residues are preferable. More preferable materials are wood, paddy straw, old rice, corn, sugar cane, cassava, sago palm, potatoes, fat, old papers, papermaking residues and the like and most preferable materials are corn, sugar cane, cassava and sago palm.

The biomass materials generally contain nitrogen atom, many alkali metals and alkaline earth metals such as Na, K, Mg and Ca.

These biomass materials are induced to carbon sources through a known pretreatment/saccharification step and the like, such as chemical treatment using an acid, an alkali or the like, biological treatment using a microorganism and physical treatment, although the method is not particularly limited. The step often includes a step for reducing the size through pretreatment for chipping, shaving or mashing the biomass material, and if necessary, further includes a pulverization step using a grinder or a mill.

The biomass material which has been thus reduced in size is generally induced to a carbon source through a further pretreatment/saccharification step. Examples of the specific method are: chemical methods such as acid treatment using a strong acid such as sulfuric acid, nitric acid, hydrochloric acid or phosphoric acid, alkali treatment, ammonia freezing steam blasting method, extraction with a solvent, supercritical fluid treatment and treatment with an oxidizing agent; physical methods such as pulverization, steam blasting method, microwave treatment and irradiation with electron beams; and biological treatment such as hydrolysis by treatment with a microorganism or an enzyme.

In general, as the carbon source induced from the above biomass materials, following fermentative carbohydrates and the like are used: hexoses such as glucose, mannose, galactose, fructose, sorbose and tagatose; pentoses such as arabinose, xylose, ribose, xylulose and ribulose; di- and polysaccharides such as pentosan, saccharose, starch and cellulose; fat such as butyric acid, caproic acid, caprylic acid, capric acid, lauric acid, myristic acid, palmitic acid, palmitoleic acid, stearic acid, oleic acid, linoleic acid, linolenic acid, monocutinic acid, arachidic acid, eicosenoic acid, arachidonic acid, behenic acid, erucic acid, docosapentaenoic acid, docosahexaenoic acid, lignoceric acid and selacholeic acid; and polyalcohols such as glycerin, mannitol, xylitol and ribitol. Among them, hexoses, pentoses or disaccharides such as glucose, fructose, xylose or saccharose is preferable and glucose is particularly preferable. Cellulose, which is the main component of papers, is also preferable as the plant-derived carbon source in a broader sense.

In general, the raw material 1,4-BG is synthesized from these carbon sources, by a fermentation method by microbial conversion, a chemical conversion method including a reaction step such as hydrolysis, dehydration reaction, hydration reaction or oxidation reaction, and a combination of the fermentation method and the chemical conversion method. Among these methods, the fermentation method by microbial conversion is preferable.

The microorganism used in the fermentation method by microbial conversion is not particularly limited and examples thereof are coryneform bacteria, *Escherichia coli, Anaerobiospirillum, Actinobacillus*, filamentous fungi and yeast. Among the above microorganisms, coryneform bacteria, *Escherichia coli, Anaerobiospirillum* and yeast are preferable and coryneform bacteria, *Escherichia coli* and yeast are more preferable. *Escherichia coli* is particularly preferable.

In case of the fermentation method by microbial conversion, because the raw material 1,4-BG can be produced efficiently, the microbial conversion is particularly preferably the conversion using a non-natural microorganism biocatalyst, and it is preferable to use a non-natural microorganism biocatalyst which contains a microorganism containing at least one extrinsic nucleic acid fragment coding 4-hydroxybutanoic acid dehydrogenase, succinyl-CoA synthetase, CoA-dependent succinate-semialdehyde dehydrogenase or α-ketoglutarate decarboxylase and having 4-hydroxybutanoic acid biosynthesis pathway and in which the microorganism contains the extrinsic nucleic acid fragment in an amount sufficient to secrete a monomer of 4-hydroxybutanoic acid.

The biomass-derived raw material 1,4-BG used in the invention may be produced directly by the fermentation method from the above-described carbon sources such as glucose, fructose, xylose and saccharose, or may be obtained by converting succinic acid, succinic anhydride, succinic acid ester, gamma butyrolactone, a derivative thereof and the like obtained by the fermentation method into 1,4-BG by chemical reaction. Alternatively, 1,4-BG may be produced from propylene, butadiene, butane, acetylene, synthetic gas or the like obtained by the fermentation method. Among these methods, the method in which the raw material 1,4-BG is directly obtained by the fermentation method is efficient and thus preferable.

Examples of the reduction catalyst for hydrogenating succinic acid are Pd, Ru, Re, Rh, Ni, Cu, Co and a compound thereof. Specifically, Pd/Ag/Re, Ru/Ni/Co/ZnO, Cu/Zn oxide, Cu/Zn/Cr oxide, Ru/Re, Re/C, Ru/Sn, Ru/Pt/Sn, Pt/Re/alkali, Pt/Re, Pd/Co/Re, Cu/Si, Cu/Cr/Mn, ReO/CuO/ZnO, CuO/CrO, Pd/Re, Ni/Co, Pd/CuO/CrO$_3$, Ru phosphate, Ni/Co, Co/Ru/Mn, Cu/Pd/KOH, Cu/Cr/Zn and the like are mentioned. Among them, Ru/Sn or Ru/Pt/Sn is preferable in view of the active point of the catalyst.

In addition, a method for producing the raw material 1,4-BG from the biomass material using a combination with known catalytic reaction in organic chemistry is also used. For example, when pentose is used as the biomass material, the raw material 1,4-BG can be easily produced by a combination of known dehydration reaction and catalytic reaction.

The raw material 1,4-BG induced from the biomass material contains a nitrogen-containing compound as impurities due to fermentation treatment and purification treatment including a step for neutralizing an acid. Specifically, a nitrogen-containing compound derived from an amino acid, a protein, ammonia, urea, or a fermentative bacterium is contained.

In the raw material 1,4-BG obtained from the biomass material, which serves as the raw material of PBT in the invention, the upper limit of the nitrogen content is generally 50 ppm, preferably 20 ppm, further preferably 10 ppm and more preferably 5 ppm, in terms of the mass ratio to the raw material 1,4-BG. The lower limit thereof is generally 0.01 ppm and preferably 0.1 ppm, and the lower limit is particularly preferably 0.2 ppm in view of the economic efficiency of the purification step.

The lower the nitrogen content in the raw material 1,4-BG, the more likely the produced PBT is to have preferable color and the like. On the other hand, a higher content is economically advantageous because the purification step becomes simpler and the degree of conversion of 1,4-BG into THF can be kept low during the PBT production reaction.

In the invention, the nitrogen content in 1,4-BG can be measured by the method described in the Examples below, but the measuring method is not limited to the method.

It is not clear why the rate of polycondensation reaction, the color and the like tend to be preferable when the nitrogen content in the raw material 1,4-BG used for producing PBT in the invention is 0.01 to 50 ppm by mass. However, it is speculated that this is because the production of a coloration-inducing substance which inhibits the polycondensation reaction and deteriorates the color of PBT like the nitrogen-containing compound can be prevented, during the purification step which contains treatment and distillation of the fermentation solution and which is for controlling the nitrogen content in the raw material 1,4-BG.

For example, GBL is contained in the raw material 1,4-BG used in the invention. GBL is thought to produce derivatives of the nitrogen-containing compound and various amides, amines, amino acids and the like and the derivatives are highly-reactive, bi- or multifunctional components. Thus, it is thought that a component which remarkably deteriorates the color of PBT is included in these derivatives.

Regarding the nitrogen content in the biomass-derived raw material 1,4-BG, when the raw material 1,4-BG is obtained by hydrogenating succinic acid obtained by fermentation of the biomass material, for example, the amount of the nitrogen-containing compound in succinic acid can be controlled by the condition for fermentation, the condition for neutralization with ammonia, the condition for crystallization of succinic acid or the like. The nitrogen content in 1,4-BG obtained by hydrogenating succinic acid can be controlled by the condition for purification including distillation. In addition, when the raw material 1,4-BG is obtained directly by fermentation of the biomass material, the nitrogen content can be controlled by the condition for fermentation, the condition for neutralization with ammonia, the condition for purification including distillation of the obtained 1,4-BG or the like.

The biomass-derived raw material 1,4-BG generally contains GBL as impurities. For example, when the raw material 1,4-BG is produced by hydrogenation via maleic acid, succinic acid, succinic anhydride, succinic acid ester or the like as an intermediate, or when 2-hydroxytetrahydrofuran is contained as impurities and the dehydrogenation of 2-hydroxytetrahydrofuran progresses, the raw material 1,4-BG contains GBL as impurities. Also when the raw material 1,4-BG is obtained directly by the fermentation method from the biomass material, it is thought that the hydrogenation of maleic acid, succinic acid, succinic anhydride, succinic acid ester or the like progresses in the fermenter and GBL is generated as a by-product.

When the raw material 1,4-BG used for producing PBT in the invention is crude 1,4-BG containing a large amount of GBL generated as a by-product as explained above, the crude 1,4-BG may be purified to obtain the raw material 1,4-BG. In the crude 1,4-BG, the upper limit of the GBL content is generally 2% by mass, preferably 1% by mass, further preferably 1000 ppm, particularly preferably 200 ppm and most preferably 180 ppm, in terms of the mass ratio to the crude 1,4-BG. The lower limit thereof is generally 101 ppm and preferably 120 ppm, and the lower limit is particularly preferably 150 ppm in view of the economic efficiency of the fermentation step and the hydrogenation step.

In the biomass-derived raw material 1,4-BG used for producing PBT in the invention, the upper limit of the GBL content is generally 100 ppm, preferably 50 ppm, further preferably 40 ppm, particularly preferably 30 ppm and most preferably 20 ppm, in terms of the mass ratio to the raw material 1,4-BG. The lower limit thereof is generally 1 ppm and preferably 2 ppm, and the lower limit is particularly preferably 5 ppm in view of the economic efficiency of the purification step.

The lower the GBL content in the raw material 1,4-BG containing the nitrogen-containing compound, the more likely the rate of polycondensation reaction during the PBT production and the color of the produced PBT are to be preferable. On the other hand, a higher content is economically advantageous because the purification step becomes simpler. In the invention, the color of the obtained PBT can be adjusted by controlling the GBL content in the raw material 1,4-BG in the above range.

In this regard, the GBL content in the raw material 1,4-BG or the crude 1,4-BG is measured by the method described in the Examples below.

It is not clear why the rate of polycondensation reaction and the color tend to be preferable when the GBL content in the biomass-derived raw material 1,4-BG used for producing PBT in this invention is 1 to 100 ppm by mass. However, as described above, this is thought to be because it is possible to reduce the amounts of the highly-reactive, bi- or multifunctional derivatives of various amides, amines, amino acids and the like, which are thought to be generated by the reaction of GBL and the nitrogen-containing component and which are thought to be the cause for the deterioration of the PBT color.

Regarding the GBL content in the biomass-derived raw material 1,4-BG, when the raw material 1,4-BG is obtained by hydrogenating succinic acid obtained by fermentation of the biomass material, for example, the GBL content in succinic acid can be controlled by the condition for fermentation, the condition for neutralization with ammonia, the condition for crystallization of succinic acid or the like. However, during the hydrogenation of succinic acid, GBL is an intermediate for synthesizing 1,4-BG and it is difficult to control the GBL content accurately. Thus, it is preferable to control the GBL content in the raw material 1,4-BG by previously purifying the biomass-derived raw material 1,4-BG before introducing the material into the reactor for producing PBT.

In this case, GBL is a component with a lower boiling point than that of 1,4-BG and thus the GBL content in the raw material 1,4-BG can be controlled by separating the components with a low boiling point by distillation during the purification step of 1,4-BG.

In addition, when 1,4-BG is produced directly by fermentation of the biomass material, the GBL content can be controlled by the condition for fermentation, the condition for neutralization with ammonia, the condition for purification including distillation of the obtained crude 1,4-BG or the like. Also in this case, removal of the components with a low boiling point including GBL by purifying the crude 1,4-BG is a preferable means.

In general, the separation of GBL and the crude 1,4-BG by distillation can be conducted by multistage distillation using a filler and/or a tray. Here, GBL can be evaporated from the top part of the separation distillation column, but GBL reacts with 1,4-BG and have a high boiling point under a high-temperature condition. The component with a high boiling point degrades to produce GBL in the next step, and thus it is preferable to reduce the generation of the component with a high boiling point from the component with a low boiling point in the separation distillation column.

From such a viewpoint, the temperature at the top part of the separation distillation column is within the range of generally preferably 40 to 180° C., further preferably 50 to 160° C. and particularly preferably 60 to 150° C. The temperature at the top part not lower than the lower limit is economically advantageous because cooling with water becomes easy. On the other hand, the temperature not higher than the above upper limit prevents the generation of the component with a high boiling point from remarkably accelerated, and thus such a temperature is preferable.

In addition, in the biomass-derived raw material 1,4-BG used for producing PBT in the invention, the upper limit of the 1-acetoxy-4-hydroxybutane (1,4-HAB) content is preferably 99 ppm, further preferably 90 ppm, particularly preferably 80 ppm and most preferably 70 ppm, in terms of the mass ratio to the raw material 1,4-BG. The lower limit thereof is preferably 1 ppm and further preferably 2 ppm, and the lower limit is particularly preferably 5 ppm in view of the economic efficiency of the purification step. The lower the 1,4-HAB content in 1,4-BG containing the nitrogen-containing compound, the more likely the rate of polycondensation reaction during the PBT production and the color of the produced PBT are to be preferable. On the other hand, a higher content is economically advantageous because the purification step becomes simpler.

The 1,4-HAB content in the raw material 1,4-BG is measured by the method described in the Examples below.

When the raw material 1,4-BG is obtained by hydrogenating succinic acid obtained by fermentation of the biomass material, for example, the 1,4-HAB content in the biomass-derived raw material 1,4-BG can be controlled also by controlling the 1,4-HAB content in succinic acid by the condition for fermentation, the condition for neutralization with ammonia, the condition for crystallization of succinic acid or the like. However, it is preferable to control the 1,4-HAB content in the raw material 1,4-BG by previously purifying the biomass-derived crude 1,4-BG before introducing the material into the reactor for producing PBT.

In this case, 1,4-HAB is a component with a lower boiling point than that of 1,4-BG and thus the 1,4-HAB content in the raw material 1,4-BG can be controlled by separating the components with a low boiling point by distillation during the purification step of the crude 1,4-BG.

In addition, when 1,4-BG is obtained directly by fermentation of the biomass material, the 1,4-HAB content can be controlled by the condition for fermentation, the condition for neutralization with ammonia, the condition for purification including distillation of the obtained 1,4-BG or the like. Also in this case, removal of the components with a low boiling point including 1,4-HAB by purifying the crude 1,4-BG is a preferable means.

The separation of 1,4-HAB and the crude 1,4-BG by distillation can be conducted at the same time with the separation of GBL and the crude 1,4-BG by distillation described above.

<PBT Production>

The method for producing PBT of the invention is not particularly limited as long as PBT can be produced.

Known methods for producing PBT are roughly classified into a so-called direct polymerization method using terephthalic acid as the main raw material and an ester-exchange method using alkyl terephthalate as the main raw material. The former method produces water in the initial esterification reaction while the latter method produces alcohol in the initial ester-exchange reaction. The direct polymerization method is preferable, because the raw materials are stably obtained, it is easy to treat the distillate and the basic unit of the raw materials is high, and also in view of the improvement effect according to the invention.

An example of the direct polymerization method is as follows. A dicarboxylic acid component containing terephthalic acid and a diol component containing the raw material 1,4-BG are reacted in a single-stage or multistage esterification reactor in the presence of an esterification catalyst. The temperature is generally 180° C. or higher, preferably 200° C. or higher and particularly preferably 210° C. or higher, and generally 260° C. or lower, preferably 250° C. or lower and particularly preferably 245° C. or lower. The pressure is generally 10 kPa or higher, preferably 13 kPa or higher and particularly preferably 50 kPa or higher, and generally 133 kPa or lower, preferably 120 kPa or lower and particularly preferably 110 kPa or lower. The reaction period is generally 0.5 hours or longer and preferably 1 hour or longer, and generally 5 hours or shorter and preferably 3 hours or shorter.

Under the above condition, esterification reaction is conducted continuously, and the oligomer obtained as the esterification product is sent to a polycondensation reactor. Then, polycondensation reaction is conducted continuously in multistage polycondensation reactors in the presence of a polycondensation catalyst. The reaction temperature is generally 210° C. or higher and preferably 220° C. or higher, and generally 260° C. or lower, preferably 250° C. or lower and particularly preferably 245° C. or lower. The pressure is generally 27 kPa or lower, preferably 20 kPa or lower and more preferably 13 kPa or lower; and in particular, the pressure is preferably 2 kPa or lower in at least one polycondensation reactor. Under reduced pressure under the above condition, polycondensation reaction is conducted generally for 2 to 12 hours and preferably for 2 to 10 hours, while stiffing the material. This method or the like is an example of the direct polymerization method.

An example of the ester-exchange method is as follows. A dicarboxylic acid component containing a terephthalic acid ester such as dimethyl terephthalate and a diol component containing the raw material 1,4-BG are reacted in a single-stage or multistage esterification reactor in the presence of an ester-exchange catalyst. The temperature is generally 110° C. or higher, preferably 140° C. or higher and particularly preferably 180° C. or higher, and generally 260° C. or lower, preferably 245° C. or lower and particularly preferably 220° C. or lower. The pressure is generally 10 kPa or higher, preferably 13 kPa or higher and particularly preferably 60 kPa or higher, and generally 133 kPa or lower, preferably 120 kPa or lower and particularly preferably 110 kPa or lower. The reaction period is generally 0.5 hours or longer and preferably 1 hour or longer, and generally 5 hours or shorter and preferably 3 hours or shorter.

Under the above condition, ester-exchange reaction is conducted continuously, and the oligomer obtained as the ester-exchanged product is sent to a polycondensation reactor. Then, polycondensation reaction is conducted continuously in multistage polycondensation reactors in the presence of a polycondensation catalyst. The reaction temperature is generally 210° C. or higher and preferably 220° C. or higher, and generally 260° C. or lower, preferably 250° C. or lower and particularly preferably 245° C. or lower. The pressure is generally 27 kPa or lower, preferably 20 kPa or lower and more preferably 13 kPa or lower; and in particular, the pressure is preferably 2 kPa or lower in at least one polycondensation reactor. Under reduced pressure under the above condition, polycondensation reaction is conducted generally for 2 to 12 hours and preferably for 2 to 10 hours, while stirring the material. This method or the like is an example of the ester-exchange method.

Examples of the esterification catalyst or the ester-exchange catalyst are: antimony compounds such as antimony trioxide; germanium compounds such as germanium dioxide and germanium tetraoxide; titanium compounds including titanium alcoholate such as tetramethyl titanate, tetraisopropyl titanate and tetrabutyl titanate, and titanium phenolate such as tetraphenyl titanate; tin compounds such as dibutyltin oxide, methylphenyltin oxide, tetraethyltin, hexaethylditin oxide, cyclohexahexylditin oxide, didodecyltin oxide, triethyltin hydroxide, triphenyltin hydroxide, triisobutyltin acetate, dibutyltin diacetate, diphenyltin dilaurate, monobutyltin trichloride, tributyltin chloride, dibutyltin sulfide, butylhydroxytin oxide, methylstannoic acid, ethylstannoic acid and butylstannoic acid; magnesium compounds such as magnesium acetate, magnesium hydroxide, magnesium carbonate, magnesium oxide, magnesium alkoxide and magnesium hydrogen phosphate; and alkaline earth metal compounds including calcium compounds such as calcium acetate, calcium hydroxide, calcium carbonate, calcium oxide, calcium alkoxide and calcium hydrogen phosphate, as well as manganese compounds and zinc compounds. A kind of these catalysts may be used alone or a mixture of two or more kinds thereof may be used. Among them, titanium compounds and tin compounds are preferable and tetrabutyl titanate is particularly preferable.

The amount of the esterification catalyst or the ester-exchange catalyst is not particularly limited. However, in terms of the metal concentration (mass) in PBT, the amount is generally 1 ppm or more, preferably 5 ppm or more, further preferably 10 ppm or more, particularly preferably 20 ppm or more and most preferably 30 ppm or more; and the amount is generally 300 ppm or less, preferably 200 ppm or less, more preferably 150 ppm or less, further preferably 100 ppm or less, particularly preferably 90 ppm or less and most preferably 60 ppm or less. When the metal concentration (mass) in PBT is not higher than the above upper limit, the catalyst is unlikely to become foreign materials and the deterioration reaction and the gas generation during the thermal retention of PBT are unlikely to occur, while the rate of the main reaction is high and the side reaction is unlikely to occur when the concentration is not lower than the above lower limit.

In addition, the esterification catalyst or the ester-exchange catalyst may be used as it is as the polycondensation catalyst, or the above-described catalyst may be further added as the polycondensation catalyst. The amount of the polycondensation catalyst is not particularly limited. However, from the same reason as for the esterification catalyst or the ester-exchange catalyst above, the amount in terms of the metal concentration (mass) in PBT is generally 0.5 ppm or more, preferably 1 ppm or more, further preferably 3 ppm or more, particularly preferably 5 ppm or more and most preferably 10 ppm or more; and the amount is generally 300 ppm or less, preferably 200 ppm or less, further preferably 100 ppm or less, particularly preferably 50 ppm or less and most preferably 30 ppm or less.

Moreover, when an organic titanium compound is used as the catalyst, from the viewpoint of preventing foreign materials, the final titanium metal concentration (mass) in PBT is preferably 250 ppm or less, further preferably 100 ppm or less, particularly preferably 60 ppm or less and most preferably 50 ppm or less.

The metal concentrations (mass) in PBT can be measured by the atomic emission method, induced coupled plasma (ICP) method or the like after recovering the metals in PBT by the wet ashing method or the like.

Furthermore, in the esterification reaction, the ester-exchange reaction and the polycondensation reaction, the following materials may be used in addition to the above catalysts: phosphorous compounds such as orthophosphoric acid, phosphorous acid, hypophosphorous acid, polyphosphoric acid, esters thereof and metal salts thereof; auxiliary agents, for example, alkali metal compounds including sodium compounds such as sodium hydroxide and sodium benzoate, lithium compounds such as lithium acetate, and potassium compounds such as potassium hydroxide and potassium acetate; auxiliary agents, for example, alkaline earth metal compounds such as magnesium acetate and calcium acetate; phenol compounds such as 2,6-di-t-butyl- 4-octylphenol and pentaerythrityl-tetrakis[3-(3',5'-t-butyl-4'-hydroxyphenyl)propionate]; thioether compounds such as dilauryl-3,3'-thiodipropionate and pentaerythrityl-tetrakis(3-laurylthiodipropionate); antioxidants, for example, phosphorous compounds such as triphenyl phosphite, tris(nonylphenyl)phosphite and tris(2,4-di-t-butylphenyl)phosphite; long-chain fatty acids and esters thereof represented by paraffin wax, microcrystalline wax, polyethylene wax, montanic acid and montanic acid ester; mold release agents such as silicone oil; and the like.

As the polycondensation reactor, known reactors such as a vertical stirring polymerization reactor, a horizontal stirring polymerization reactor and a thin-film evaporation polymerization reactor are mentioned. At a later stage of the polycondensation where the viscosity of the reaction liquid increases, the transfer of materials, rather than the reaction rate, tends to be the factor for governing the increase in the molecular weight. Thus, in order to advance the main reaction while inhibiting the side reaction, lowering the temperature as much as possible and enhancing the surface renewal property are effective in achieving the object of the invention. It is thus preferable to choose one or more horizontal stirring polymerization reactors with thin-film evaporation property and excellent in the surface renewal property, plug flow property and self-cleaning property.

In addition, it is also possible to increase the molecular weight of the PBT obtained by the production method of the invention by further conducting solid-state polycondensation by a known method.

The PBT obtained by the polycondensation reaction is generally sent to a polymer-extraction die from the bottom of the polycondensation reactor, extracted in a strand form, and cut into pellet or chip particles with a cutter while being cooled with water or after being cooled with water. The intrinsic viscosity of the particles can be increased by further subjecting the particles to solid-state polycondensation by a known method or the like.

<PBT>

The PBT produced in the invention (hereinafter sometimes referred to as "the PBT of the invention") contains a structural unit derived from terephthalic acid and a structural unit derived from 1,4-butanediol. The nitrogen content in 1,4-butanediol is 0.01 to 50 ppm by mass and the gamma butyrolactone content is 1 to 100 ppm by mass.

The upper limit of the nitrogen content (mass ratio) in the PBT of the invention is preferably 10 ppm and more preferably 2 ppm, and the lower limit is preferably 0.05 ppm and more preferably 0.1 ppm. Though the influence of the gamma butyrolactone content in the PBT of the invention is unknown, it is thought that gamma butyrolactone is converted into another component such as an amide, an amine, an amino acid or the like which is a cause for deteriorating the PBT color and such a component is contained in the PBT.

The PBT with the nitrogen content within the above range can be obtained using the preferable biomass-derived raw material 1,4-butanediol described above and terephthalic acid or the alkyl terephthalate as the raw materials, in accordance with the production method according to the invention described above.

The intrinsic viscosity of the PBT of the invention is not particularly limited. In view of the mechanical property, the stability of the pellet formation and the formability, the intrinsic viscosity is preferably 0.50 dL/g or more and further preferably 0.70 dL/g or more, and preferably 1.50 dL/g or less and further preferably 1.35 dL/g or less. The intrinsic viscosity of the PBT which is not less than the above lower limit tends to be preferable in view of the mechanical property of molded part, and the intrinsic viscosity not more than the above upper limit tends to be preferable in view of the formability.

The intrinsic viscosity of the PBT is measured by the method described in the Examples below.

The concentration of the terminal carboxyl group of the PBT of the invention is not particularly limited. However, the lower limit is preferably 1 equivalent/ton, further preferably 2 equivalent/ton, particularly preferably 3 equivalent/ton and most preferably 5 equivalent/ton, and the upper limit is preferably 50 equivalent/ton, further preferably 40 equivalent/ton, particularly preferably 30 equivalent/ton and most preferably 25 equivalent/ton. When the concentration of the terminal carboxyl group of the PBT is not more than the above upper limit, the resistance to hydrolysis of the PBT tends to be excellent, while the polycondensation property tends to be excellent when the concentration is not less than the above lower limit.

The concentration of the terminal carboxyl group of the PBT can be measured by dissolving the resin in an organic solvent and titrating the solution with an alkali solution such as sodium hydroxide. More specifically, the concentration is measured by the method described in the Examples below.

<Color of PBT>

In general, the color of PBT produced from biomass-derived raw material 1,4-BG tends to be deteriorated; nevertheless, the PBT of the invention has an excellent color. Moreover, as described above, by controlling the GBL content in the raw material 1,4-BG during the purification step of the crude 1,4-BG or the like, the color of the obtained PBT can be adjusted.

<PBT Composition>

The PBT of the invention may be a PBT composition containing components other than the PBT as long as the effects of the invention are not largely impaired. Specific examples of the components other than the PBT are various resins such as a thermoplastic resin and a thermosetting resin, a mold release agent, fillers such as a reinforcing filler, a flame retardant and other various additives.

As the thermoplastic resin, polyethylene, polypropylene, polystyrene, polyacrylonitrile, polymethacrylic ester, polyacrylic ester, ABS resin, polycarbonate, polyamide, polyphenylene sulfide, polyethylene terephthalate, liquid crystal polyester, polyacetal, polyphenyleneoxide and the like are mentioned. As the thermosetting resin, a phenolic resin, a melamine resin, a silicone resin, an epoxy resin and the like are mentioned. A kind of these resins may be used alone or a combination of two or more kinds thereof may be used. Among them, the thermoplastic resin is often used.

When the resin is incorporated, the amount (mass) thereof is not particularly limited as long as the excellent effects of the invention are achieved. However, the amount is adjusted in such a way that the proportion of the PBT to the total resin amount is generally 0.1% by mass or more, preferably 1% by mass or more and further preferably 10% by mass or more, and generally 99.9% by mass or less, preferably 99% by mass or less and further preferably 90% by mass or less.

The mold release agent is not particularly limited but examples thereof are: phenol compounds such as 2,6-di-t-butyl-4-octylphenol and pentaerythrityl-tetrakis[3-(3',5'-t-butyl-4'-hydroxyphenyl)propionate]; thioether compounds such as dilauryl-3,3'-thiodipropionate and pentaerythrityl-tetrakis(3-laurylthiodipropionate); long-chain fatty acids and esters thereof represented by paraffin wax, microcrystalline wax, polyethylene wax, montanic acid and montanic acid ester; and silicone oil. A kind of these mold release agents may be used alone or a mixture of two or more kinds thereof may be used.

The reinforcing filler is not particularly limited but examples thereof are: inorganic fibers such as glass fibers, carbon fibers, silica/alumina fibers, zirconia fibers, boron fibers, boron nitride fibers, silicon nitride potassium titanate fibers and metal fibers; and organic fibers such as aromatic polyamide fibers and fluorine resin fibers. Among them, inorganic fibers, in particular glass fibers, are preferably used. A kind of the reinforcing fillers may be used alone or a combination of two or more kinds thereof may be used.

When the reinforcing filler is inorganic fibers or organic fibers, the average fiber diameter is not particularly limited but is generally 1 to 100 μm, preferably 2 to 50 μm, further preferably 3 to 30 μm and particularly preferably 5 to 20 μm. The average fiber length is not particularly limited but is generally 0.1 to 20 mm and preferably 1 to 10 mm.

In order to improve the adhesiveness at the interface with the PBT, it is preferable to use a reinforcing filler which has been subjected to surface treatment with a sizing agent or a surface treating agent. Examples of the sizing agent or the surface treating agent are functional compounds such as an epoxy compound, an acrylic compound, an isocyanate compound, a silane compound and a titanate compound. The treatment with the sizing agent or the surface treating agent may be conducted by previously subjecting the reinforcing filler to the surface treatment, or the reinforcing filler may be brought into contact with the sizing agent or the surface treating agent when the PBT composition is prepared.

When the reinforcing filler is used, the amount thereof is generally 150 parts by mass or less and preferably 5 to 100 parts by mass, relative to 100 parts by mass of the resin component containing PBT.

A filler other than the reinforcing filler may be added to the PBT of the invention. Examples of the filler are a plate-shaped inorganic filler, ceramic beads, asbestos, wollastonite, talc, clay, mica, zeolite, kaolin, potassium titanate, barium sulfate, titanium oxide, silicon oxide, aluminum oxide and magnesium hydroxide.

By incorporating the plate-shaped inorganic filler, the anisotropic degree and the warping of the molded part can be reduced. Examples of the plate-shaped inorganic filler are glass flakes, mica and a metal foil. Among them, glass flakes are preferably used.

In addition, a flame retardant may be added to the PBT of the invention to achieve flame retardancy. The flame retardant is not particularly limited but examples thereof are an organic halogen compound, an antimony compound, a phosphorous compound, other organic flame retardants and inorganic flame retardants.

Examples of the organic halogen compound are brominated polycarbonate, a brominated epoxy resin, a brominated phenoxy resin, a brominated polyphenylene ether resin, a brominated polystyrene resin, brominated bisphenol A and polypentabromobenzyl acrylate. Examples of the antimony compound are antimony trioxide, antimony pentoxide and sodium antimonate. Examples of the phosphorous compound are phosphoric ester, polyphosphoric acid, ammonium polyphosphate and red phosphorus. Examples of the other organic flame retardants are nitrogen compounds such as melamine and cyanuric acid. Examples of the other inorganic flame retardants are aluminum hydroxide, magnesium hydroxide, a silicon compound and a boron compound. A kind of these flame retardants may be used alone or a mixture of two or more kinds thereof may be used.

The other various additives are not particularly limited but examples thereof are a glidant, a catalyst deactivator, a crystal nucleating agent and a crystallization promoter in addition to an antioxidant and a stabilizer such as a heat-resistant stabilizer. These additives may be added during the polycondensation or after the polycondensation.

In addition, as the other various additives, an ultraviolet absorbing agent, a stabilizer such as a weathering stabilizer, a coloring agent such as a pigment, an antistatic agent, a foaming agent, a plasticizer, an agent for improving impact resistance and the like are also mentioned.

The method for incorporating the other components above is not particularly limited, but a preferable example is a method in which a single- or twin-screw extruder with a facility enabling the volatilization from a ventilation opening is used as a mixer. The components, including the additional components, may be supplied to the mixer at the same time or may be supplied one by one. In addition, two or more components selected from the components including the additional components may be previously mixed.

<PBT Molding>

The method for molding the PBT of the invention and the PBT composition containing the PBT is not particularly limited, and molding methods which are generally used for molding a thermoplastic resin, namely, injection molding, hollow molding, extrusion molding, press molding and the like, can be applied.

The PBT of the invention and the PBT composition containing the PBT are excellent in the color, thermal stability, transparency and quality stability, and can be preferably used for injection-molded parts such as electric or electronic parts and automotive parts, and for extrusion-molded parts such as a film, a monofilament and fibers.

EXAMPLES

The invention is explained further in detail below with Examples, but the invention is not limited by the following Examples as long as it does not go beyond the gist thereof.

[Analysis Method]

<Nitrogen Content (Ppm by Mass) in Raw Material 1,4-BG>

A sample of raw material 1,4-BG in an amount of 15 mg was placed on a plasterboard and the sample was burned using a trace total nitrogen analyzer (model "TN-10" manufactured by DIA Instruments Co., Ltd.). The nitrogen content was thus measured by the combustion/chemical emission method. Samples in which aniline was dissolved in toluene in the concentrations of 0, 0.5, 1.0 and 2.0 μg/mL in terms of nitrogen atom were also prepared and used as the standard samples.

<Contents (Ppm by Mass) of GBL and Other Components in Raw Material 1,4-BG>

Using a gas chromatography analyzer (model "Shimadzu GC-2014" manufactured by Shimadzu Corporation) with DB-1 column (non-polar type), in accordance with the corrected area percentage method, the contents of peak components such as the raw material 1,4-BG, GBL, and other components like 1,4-HAB were measured and their contents in 1,4-BG were calculated.

<Production Amounts of Water and THF During PBT Production>

The water amount in a distillate generated in the esterification reaction was measured by the Karl Fischer method (measured with "CA-03" manufactured by Mitsubishi Chemical Corporation) and the components except for the water were regarded as organic components. The THF amount in the organic components was measured by the gas chromatograph method above to obtain the production amount of THF. The production amount of THF was converted into the value (mol %) relative to terephthalic acid and this value was regarded as the degree of conversion.

<Intrinsic Viscosity (IV) of PBT>

The intrinsic viscosity was measured with the following procedures using a Ubbelohde viscometer. That is, using a mixed solvent of phenol/tetrachloroethane (mass ratio of 1/1), the periods (seconds) over which a PBT solution with a concentration of 1.0 g/dL dropped and the solvent only dropped were measured at 30° C. The intrinsic viscosity was calculated by the following equation.

$$IV=((1+4K_H\eta_{sp})^{0.5}-1)/(2K_HC)$$

Here, $\eta_{sp}=(\eta/\eta_0)-1$; $\eta$ is the period (seconds) over which the PBT solution dropped; $\eta_0$ is the period (seconds) over which the solvent dropped; C is the PBT concentration (g/dL) of the PBT solution; and $K_H$ is the Huggins constant. Here, $K_H$ was 0.33.

<Concentration (Equivalent/Ton) of Terminal Carboxyl Group of PBT>

In 25 mL of benzyl alcohol, 0.5 g of PBT was dissolved and this solution was titrated with a solution of 0.01 mol/L sodium hydroxide in benzyl alcohol. The concentration was calculated by the following equation.

Concentration of terminal carboxyl group=$(A-B)\times 0.1\times f/W$ (equivalent/ton)

Here, A is the amount (µL) of the solution of 0.01N sodium hydroxide in benzyl alcohol required for the titration; B is the amount (µL) of the solution of 0.01 mol/L sodium hydroxide in benzyl alcohol required for the titration of the blank; W is the amount (g) of the PBT sample; and f is the titer of 0.01 mol/L sodium hydroxide.

<Color of PBT (b Value)>

Pellets of PBT were filled in a cylinder cell for powder measurement with an internal diameter of 30 mm and a depth of 12 mm. Using Color Meter ZE2000 (manufactured by Nippon Denshoku Industries Co., Ltd.), the simple average value of values measured at 4 points by the reflection method while turning the measurement cell by 90° was calculated. The color was evaluated with the b value according to the Lab display system. A smaller b value means that the color is less yellowish and is excellent.

[Raw Material 1,4-BG]

As the method for directly producing raw material 1,4-BG by the fermentation method, the method described in JP-T-2010-521182 and in Examples 1 to 4 of U.S. patent application publication No. 2011/0003355 was used. By purifying the crude 1,4-butanediol obtained by this method, bio-method 1,4-butanediol (B) (hereinafter sometimes abbreviated as "bio-method (B)") was obtained.

Products which were industrially available were used as the raw material 1,4-BG of the petrifying method.

The raw material 1,4-BG obtained by the butane method (C) (hereinafter sometimes abbreviated as "butane method (C)") is obtained by hydrogenating maleic acid, succinic acid, maleic anhydride and/or fumaric acid, which are produced by oxidation of butane, as the raw materials.

The raw material 1,4-BG obtained by the butadiene method (D) (hereinafter sometimes abbreviated as "butadiene method (D)") is obtained by conducting acetoxylation reaction using butadiene, acetic acid and oxygen to obtain diacetoxybutene as an intermediate and then hydrogenating and hydrolyzing diacetoxybutene.

The raw material 1,4-BG obtained by the propylene method (E) (hereinafter sometimes abbreviated as "propylene method (E)") is obtained by oxo reaction of aryl alcohol which is obtained by oxidation of propylene.

Reference Example 1

Purification of Bio-Method (B)

A composition containing 1,4-BG was biologically produced from a fermentation medium of an organism based on the descriptions in JP-T-2010-521182, and the obtained raw material 1,4-BG of bio-method (B) was purified by the following method. The term "GBL" below means "gamma butyrolactone"; "1,4-HAB" means "1-acetoxy-4-hydroxybutane"; and "BGTF" means "2-(4-hydroxybutyloxy) tetrahydrofuran". Furthermore, "ppm" and "%" are both values based on mass. The same applies to Table-2 and Table-3 below.

The raw material 1,4-BG of bio-method (B) was obtained by the method described in U.S. patent application publication No. 2011/0003355. That is, the whole bacterial cells and salt contents, or at least a part of the bacterial cells and a part of the salt contents were removed by filtration, centrifugal separation and an ion-exchange resin. Then, water was removed by distillation and the crude 1,4-BG before purification shown in Table-1 was obtained.

The crude 1,4-BG before purification was concentrated by dehydration using a rotary evaporator made of glass. The pressure was 10.7 kPa and the internal temperature was 175° C. The distillation ratio was 10% by mass and 90% by mass of the crude 1,4-BG solution was recovered relative to the charged amount which remained in the flask.

Next, batch-type distillation was conducted using the crude 1,4-BG solution after dehydration as the raw material and using a glass apparatus to separate the solution into fractions, and components with a high boiling point and components with a low boiling point were separated from the crude 1,4-BG. Here, a multistage distillation column theoretically corresponding to a three-stage column was used. The pressure at the column top was set to 13.3 kPa and the temperature at the column bottom was controlled to 182° C. The distillation temperature rose with the removal of the components with a low boiling point and then settled at 175° C. The fraction where the temperature at the column top settled was collected as the 1,4-BG fraction. Relative to the charged amount of the raw materials, 80% by mass of the 1,4-BG fraction was recovered. The composition of the purified 1,4-BG fraction is also shown in Table-1.

TABLE 1

| Component [unit] | Before purification | After purification |
| --- | --- | --- |
| Components with a low boiling point [ppm] | 378 | 118 |
| Water [%] | 9.3 | 0.002 |
| GBL [ppm] | 103 | 0 |
| 1,4-HAB [ppm] | 184 | 2 |
| 1,4-BG [%] | 90.3 | 99.8 |
| BGTF [ppm] | 636 | 1195 |
| Components with a high boiling point [ppm] | 2699 | 242 |
| Nitrogen atom [ppm] | 42 | 4.7 |

The 1,4-BG with the composition after purification shown in Table-1 was further separated into fractions using the same batch-type distillation device and five lots of purified bio-method (B) with different GBL and nitrogen contents were obtained. These lots were named lot 1, lot 2, lot 3, lot 4 and lot 5 in the order the lots were distilled. The GBL content, the nitrogen content, the 1,4-HAB content and the BGTF content of each lot are shown in Table-2. In this regard, GBL is sometimes regenerated from the components with a high boiling point and thus the GBL contents in lots 1 to 5 shown in Table-2 are higher than the content in the 1,4-BG after purification shown in Table-1.

TABLE 2

| Component [unit] | Lot 1 | Lot 2 | Lot 3 | Lot 4 | Lot 5 |
| --- | --- | --- | --- | --- | --- |
| Nitrogen atom [ppm] | 1.0 | 2.4 | 0.6 | 1.4 | 3.5 |
| GBL [ppm] | 9 | 18 | 58 | 2 | 161 |
| BGTF [ppm] | 1100 | 1130 | 1220 | 1100 | 2100 |
| 1,4-HAB [ppm] | 46 | 25 | 123 | 10 | 100 |

[PBT Production]

Example 1

To a reaction container with a stirring device, a nitrogen-introduction port, a heating device, a thermometer, a distillation tube and an exhaust port for reducing the pressure, the following materials were charged: 113 g of terephthalic acid, 183 g of the raw material 1,4-BG of the bio-method (lot 1), and 0.7 g of the raw material 1,4-BG of the bio-method (lot 1) solution in which 6% by mass of tetrabutyl titanate as a catalyst was previously dissolved. The atmosphere of the system was made nitrogen atmosphere by nitrogen-substitution under reduced pressure. Next, while the system was stirred, the temperature was raised to 150° C. and then raised to 220° C. over an hour under the atmospheric pressure, and esterification reaction was further conducted for two hours while distilling the water produced.

Then, magnesium acetate tetrahydrate was dissolved in water, and then 1.3 g of a 1,4-BG solution obtained by dissolving 1% by mass of magnesium acetate tetrahydrate in the raw material 1,4-BG of the bio-method (lot 1) (the mass proportion of magnesium acetate tetrahydrate, water and 1,4-BG=1:2:97) was added thereto.

The solution was subsequently kept at 220° C. for 0.25 hours and then kept at 245° C. after raising the temperature to 245° C. over 0.75 hours. Here, the pressure was reduced to 0.07 kPa over 1.5 hours, after the initiation of the polymerization, and polycondensation reaction was conducted under the same reduced pressure for 0.8 hours. The pressure of the reaction system was then returned to the normal pressure and the polycondensation was finished. The obtained PBT was extracted from the bottom of the reactor in a strand form and immersed in water at 10° C. The strand was then cut with a cutter to obtain pellets of the PBT.

The period from the initiation of the pressure reduction after adding magnesium acetate to the completion of the polycondensation was regarded as the polycondensation period, and the value of intrinsic viscosity/polycondensation period was taken as the polycondensation rate. The polycondensation rate was 0.37 dL/g/hour. The THF amount in the distillate during the esterification reaction was analyzed and the degree of conversion into THF represented by mol % was 70.6% by mol relative to charged terephthalic acid.

Table-3 shows the analysis results of the obtained PBT by the above measuring methods and the GBL content, the nitrogen content, the 1,4-HAB content and the BGTF content of the bio-method (lot 1) which was used as the raw material 1,4-BG Example 2

PBT was produced in the same manner as in Example 1 except that the raw material 1,4-BG was changed to lot 2 obtained by the purification of the bio-method. Table-3 shows the degree of conversion [%] into THF during the PBT production, the polycondensation period [hour], the polycondensation rate [dL/g/hour] and the analysis results of the PBT by the above measuring methods.

Example 3

PBT was produced in the same manner as in Example 1 except that the raw material 1,4-BG was changed to lot 3 obtained by the purification of the bio-method. Table-3 shows the degree of conversion [%] into THF during the PBT production, the polycondensation period [hour], the polycondensation rate [dL/g/hour] and the analysis results of the PBT by the above measuring methods.

Example 4

PBT was produced in the same manner as in Example 1 except that the raw material 1,4-BG was changed to lot 4 obtained by the purification of the bio-method. Table-3 shows the degree of conversion [%] into THF during the PBT production, the polycondensation period [hour], the polycondensation rate [dL/g/hour] and the analysis results of the PBT by the above measuring methods.

Comparative Example 1

PBT was produced in the same manner as in Example 1 except that the raw material 1,4-BG was changed to lot 5 obtained by the purification of the bio-method. Table-3 shows the degree of conversion [%] into THF during the PBT production, the polycondensation period [hour], the polycondensation rate [dL/g/hour] and the analysis results of the PBT by the above measuring methods.

Comparative Example 2

PBT was produced in the same manner as in Example 1 except that the raw material 1,4-BG was changed to the 1,4-BG of the butane method (C) with the composition shown in Table-3. Table-3 shows the degree of conversion [%] into THF during the PBT production, the polycondensation period [hour], the polycondensation rate [dL/g/hour] and the analysis results of the PBT by the above measuring methods.

Comparative Example 3

PBT was produced in the same manner as in Example 1 except that the raw material 1,4-BG was changed to the 1,4-BG of the butadiene method (D) with the composition shown in Table-3. Table-3 shows the degree of conversion [%] into THF during the PBT production, the polycondensation period [hour], the polycondensation rate [dL/g/hour] and the analysis results of the PBT by the above measuring methods.

Comparative Example 4

PBT was produced in the same manner as in Example 1 except that the raw material 1,4-BG was changed to the 1,4-BG of the propylene method (E) with the composition shown in Table-3. Table-3 shows the degree of conversion [%] into THF during the PBT production, the polycondensation period [hour], the polycondensation rate [dL/g/hour] and the analysis results of the PBT by the above measuring methods.

GBL, the compound which newly generates by the reaction between the nitrogen-containing compound and GBL in the biomass-derived 1,4-BG induces the coloration.

TABLE 3

|  |  | Example 1 | Example 2 | Example 3 | Example 4 |
|---|---|---|---|---|---|
| Raw material 1,4-BG | Name | Bio-method (B) (lot 1) | Bio-method (B) (lot 2) | Bio-method (B) (lot 3) | Bio-method (B) (lot 4) |
|  | Production method | Direct fermentation | Direct fermentation | Direct fermentation | Direct fermentation |
|  | Nitrogen content [ppm] | 1.0 | 2.4 | 0.6 | 1.4 |
|  | GBL content [ppm] | 9 | 18 | 58 | 2 |
|  | BGTF content [ppm] | 1100 | 1130 | 1220 | 1100 |
|  | 1,4-HAB content [ppm] | 46 | 25 | 123 | 10 |
| PBT production | Degree of conversion into THF [%] | 70.6 | 61.1 | 63.3 | 64.2 |
|  | Polycondensation period [hour] | 2.3 | 2.3 | 2.3 | 2.3 |
|  | Polycondensation rate [dL/g/hour] | 0.37 | 0.38 | 0.37 | 0.37 |
| Physical properties of PBT | Color (b value) | 1.6 | 2.1 | 2.5 | 1.1 |
|  | Intrinsic viscosity [dL/g] | 0.85 | 0.87 | 0.84 | 0.85 |
|  | Terminal carboxyl group concentration (equivalent/ton) | 7 | 7 | 5 | 4 |
|  |  | Comparative Example 1 | Comparative Example 2 | Comparative Example 3 | Comparative Example 4 |
| Raw material 1,4-BG* | Name | Bio-method (B) (lot 5) | Butane method (C) | Butadiene method (D) | Propylene method (E) |
|  | Production method | Direct fermentation | Petroleum-derived | Petroleum-derived | Petroleum-derived |
|  | Nitrogen content [ppm] | 3.5 | ND | ND | ND |
|  | GBL content [ppm] | 161 | 200 | <1 | 30 |
|  | BGTF content [ppm] | 2100 | 1350 | 1010 | 1210 |
|  | 1,4-HAB content [ppm] | 100 | 90 | 347 | ND |
| PBT production | Degree of conversion into THF [%] | 59.1 | 66 | 67.3 | 75.1 |
|  | Polycondensation period [hour] | 2.4 | 2.7 | 2.7 | 2.4 |
|  | Polycondensation rate [dL/g/hour] | 0.35 | 0.31 | 0.31 | 0.35 |
| Physical properties of PBT | Color (b value) | 4.8 | 1.7 | 1.2 | 1.9 |
|  | Intrinsic viscosity [dL/g] | 0.83 | 0.85 | 0.85 | 0.84 |
|  | Terminal carboxyl group concentration (equivalent/ton) | 4 | 10 | 9 | 11 |

*ND: For the nitrogen content, less than 0.1 ppm. For the 1,4-HAB content, less than 1 ppm.

When Examples 1 to 4 are compared with Comparative Examples 2 to 4, it is understood as follows. Although the 1,4-HAB concentrations in the raw material 1,4-BG were different among Examples 1 to 4, the polycondensation periods were all 2.3 hours. On the contrary, the polycondensation periods of Comparative Examples 2 to 4 were 2.7 hours and 2.4 hours. Thus, when PBT were produced using the biomass-derived 1,4-BG, the delay in the polymerization influenced by 1,4-HAB due to the contained nitrogen-containing compound could be prevented, in comparison with the cases in which PBT were produced using the petroleum-derived 1,4-BG as the raw materials.

Comparison between Examples 1 to 4 and Comparative Example 1 indicates that the PBT were less colored even with the biomass-derived 1,4-BG (containing nitrogen atom) as long as the GBL contents in 1,4-BG were 1 to 100 ppm by mass. Thus it is understood that the coloration due to the reaction product of the nitrogen-containing compound and GBL could be prevented.

FIG. 1 is a graph showing the color b vale of PBT against the GBL content in raw material 1,4-BG of Examples 2 to 4 and Comparative Example 1, and the color b vale of PBT against the GBL content in raw material 1,4-BG of Comparative Examples 2 to 4. From FIG. 1, no correlation can be found between the GBL concentration and the b value for 1,4-BG which did not contain nitrogen atom (Comparative Examples 2 to 4). On the other hand, there is a correlation between the GBL content and the color b value for the biomass-derived 1,4-BG containing nitrogen atom. Thus, it is speculated that, regarding the coloration of PBT due to Reference Example 2

PBT was synthesized under the same condition as in Comparative Example 3 except that 123 ppm by mass of 2-pyrrolidone (nitrogen content of 20.2 ppm by mass) was added to the raw material 1,4-BG (butadiene method (D)) used in Comparative Example 3. As a result, the color b value of the obtained PBT was 2.7, and the color b value increased by 1.5 when 123 ppm by mass of 2-pyrrolidone was added. In this regard, from the molecular weight of GBL and the molecular weight of 2-pyrrolidone, 123 ppm of 2-pyrrolidone corresponds to GBL amount of 124 ppm by mass.

In the invention, it is speculated that the component induced from GBL and the nitrogen-containing compound deteriorates the color. The deterioration in the PBT color due to 2-pyrrolidone induced from ammonia and GBL supports this speculation. It is understood that, because the component induced from GBL and the nitrogen-containing compound causes the color deterioration, the deterioration in the PBT color is not observed with the increase in the GBL content with the raw material containing no nitrogen-containing compound and containing GBL only.

In this regard, this mechanism is not limited to 2-pyrrolidone only and the nitrogen component is not limited to ammonia.

While the invention has been described in detail and with reference to specific embodiments thereof, it will be apparent to one skilled in the art that various changes and modifications can be made therein without departing from the spirit and scope of the invention. This application is based on Japanese Patent Application (Patent Application No. 2012-128064) filed on Jun. 5, 2012, the contents of which are incorporated herein by way of reference.

The invention claimed is:

1. A method for producing polybutylene terephthalate, the method comprising:
   (a) subjecting a diol component comprising a biomass-derived raw material 1,4-butanediol having a nitrogen content of from 0.01 to 20 ppm by mass and a dicarboxylic acid component comprising terephthalic acid or an alkyl terephthalate to an esterification reaction or ester-exchange reaction,
   (b) subjecting the reactant obtained in (a) to a polycondensation reaction, thereby obtaining polybutylene terephthalate, and
   further comprising directly producing the biomass-derived raw material 1,4-butanediol or a biomass-derived crude 1,4-butanediol from at least one carbon source selected from the group consisting of glucose, fructose, xylose, and saccharose by a fermentation method, and
   obtaining the biomass-derived raw material 1,4-butanediol by purifying the biomass-derived crude 1,4-butanediol before the subjecting (a),
   wherein a content of gamma butyrolactone in the biomass-derived raw material 1,4-butanediol is from 1 to 100 ppm by mass.

2. The method according to claim 1, wherein the content of gamma butyrolactone in the crude 1,4-butanediol is from 101 ppm by mass to 2% by mass.

3. The method according to claim 1, wherein a content of 1-acetoxy-4-hydroxybutane in the raw material 1,4-butanediol is from 1 to 99 ppm by mass.

4. The method according to claim 1, further comprising producing the biomass-derived raw material 1,4-butanediol or the biomass-derived crude 1,4-butanediol from a biomass material using a non-natural microorganism biocatalyst, wherein the non-natural microorganism biocatalyst comprises a microorganism containing at least one exogenous nucleic acid fragment coding 4-hydroxybutanoic acid dehydrogenase, succinyl-CoA synthetase, CoA-dependent succinate-semialdehyde dehydrogenase or α-ketoglutarate decarboxylase and having a 4-hydroxybutanoic acid biosynthesis pathway and in which the microorganism comprises the exogenous nucleic acid fragment in an amount sufficient to secrete a monomer of 4-hydroxybutanoic acid.

5. The method according to claim 1, wherein a content of the terephthalic acid or alkyl terephthalate based on the total of the dicarboxylic acid component is 80 mol % or more.

6. The method according to claim 1, wherein a content of the biomass-derived raw material 1,4-butanediol is 80 mol % or more based on the total of the diol component.

7. The method according to claim 1, wherein the dicarboxylic acid component further comprises at least one other dicarboxylic acid.

8. The method according to claim 1, wherein the diol component further comprises at least one other diol.

9. The method according to claim 4, wherein the microorganism is selected from the group consisting of *Escherichia coli, Anaerobiospirillum, Actinobacillus,* filamentous fungi and yeast.

10. The method according to claim 1, wherein the content of nitrogen in the biomass-derived raw material 1,4-butanediol is from 0.1 to 5 ppm by mass.

11. The method according to claim 1, wherein the content of the gamma butyrolactone in the biomass-derived raw material 1,4-butanediol is from 1 to 50 ppm by mass.

12. The method according to claim 1, wherein the content of the gamma butyrolactone in the biomass-derived raw material 1,4-butanediol is from 5 to 20 ppm by mass.

13. The method according to claim 1, wherein the content of the gamma butyrolactone in the biomass-derived raw material 1,4-butanediol is from 150 ppm to 2% by mass.

14. The method according to claim 4, wherein the content of 1-acetoxy-4-hydroxybutane in the raw material 1,4-butanediol is from 5 to 80ppm by mass.

15. The method according to claim 1, wherein the polycondensation reaction is conducted at a temperature from 180° C. to 260° C. and a pressure from 10 kPa to 133 kPa for 0.5 hours to 5 hours in the presence of an esterification catalyst in a single step or multiple steps.

* * * * *